United States Patent [19]

Marshall

[11] 4,285,344
[45] Aug. 25, 1981

[54] SURGICAL SCISSORS

[76] Inventor: Warren S. Marshall, 1025 Secor Rd., Toledo, Ohio 43607

[21] Appl. No.: 123,111

[22] Filed: Feb. 21, 1980

[51] Int. Cl.³ .............................................. A61B 17/32
[52] U.S. Cl. ..................................... 128/318; 30/257; 433/144; 433/159
[58] Field of Search ...................... 128/318, 91 A, 305; 30/254, 257, 259, 226, 120, 428; D8/57; 7/135, 161; 433/144, 145, 160, 159

[56] References Cited

U.S. PATENT DOCUMENTS

| | | | |
|---|---|---|---|
| 1,359,164 | 11/1920 | Lo Giudice et al. | 128/305 |
| 2,136,414 | 11/1938 | Clements | 128/318 |
| 3,365,798 | 1/1968 | Cunningham | 128/91 A |

OTHER PUBLICATIONS

*Surgery*, vol. 54 #5, Nov. 1963, pp. 745–751, Haimovici, M.D.

*Primary Examiner*—Robert W. Michell
*Assistant Examiner*—Michael H. Thaler
*Attorney, Agent, or Firm*—C. O. Marshall, Jr.

[57] ABSTRACT

A surgical scissors for excising tissue in areas of limited access where straight scissors cannot reach. The scissors has a hook-shaped end with cutting blades on a cutting axis which is generally perpendicular to the axis along which handle members of the scissors extend. The hook-shaped end may carry a second pair of cutting blades in a cutting plane which is generally parallel to the axis along which the handle members extend.

3 Claims, 4 Drawing Figures

SURGICAL SCISSORS

BACKGROUND OF THE INVENTION

The invention relates to surgical scissors and more particularly to an improved surgical scissors which is well suited to excise tissue in areas of limited access such as the oral cavity. When tissue in the third molar area cannot be properly trimmed or sutures cut due to their position, for example, reverse cutting blades are used while the handles of the scissors are held horizontally in the mouth. Also, for example, in the retromolar pad area which is almost vertical additional cutting blades are used having a cutting axis which is generally perpendicular to the axis along which the handles of the scissors extend.

An object of the invention is to provide improved surgical scissors.

Another object is to provide a reverse surgical scissors.

Still another object is to provide a surgical scissors having cutting blades with a cutting axis generally perpendicular to the axis along which the handles of the scissors extend.

A further object is to provide a reverse surgical scissors with a pair of cutting blades one generally perpendicular and one generally parallel to the axis along which the handles of the scissors extend.

Other objects and advantages of the invention will become apparent from the following detailed description, with reference being made to the accompanying drawings:

DESCRIPTION OF THE PREFERRED EMBODIMENT

Figure 1:
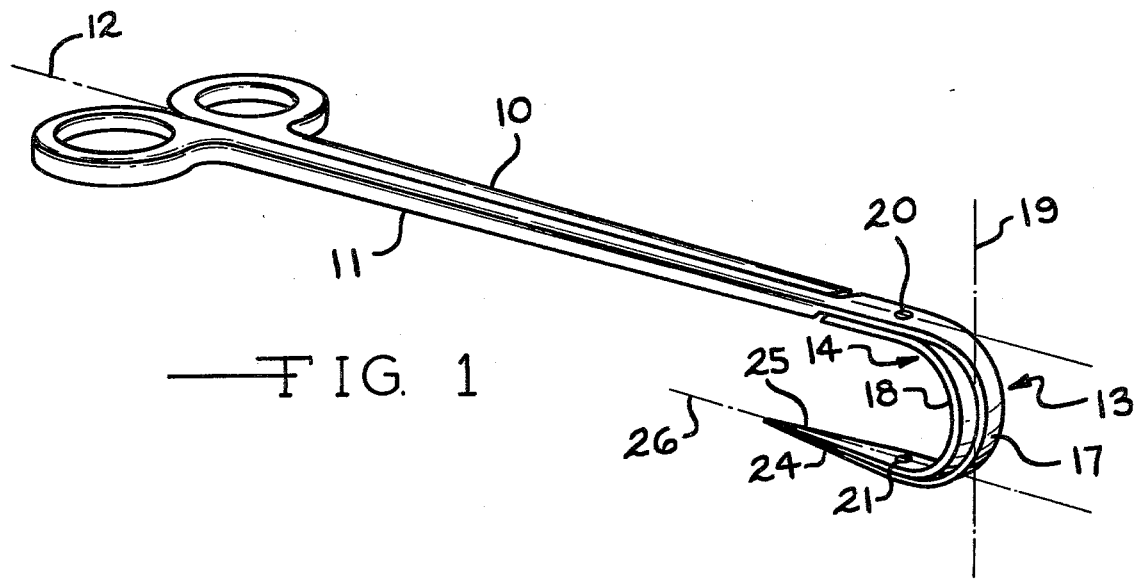
FIG. 1 is perspective view of an improved surgical scissors according to the invention.

The surgical scissors is a reverse snipping instrument having handle members 10 and 11 extending along an axis 12. The handle members 10 and 11 have hook-shaped ends 13 and 14, respectively, which are turned back upon the members in a reverse manner. The hooked-shaped ends 13 and 14 have cutting edges 15 and 16, respectively, which cooperate to form cutting blades 17 and 18, respectively, on a cutting axis 19 that is generally perpendicular to the axis 12. The cutting surfaces 15 and 16 are on the inside of the cutting blades 17 and 18 as on conventional straight scissors. Two aligned pivots 20 and 21 pivotally connect the hook-shaped ends 13 and 14.

Figure 2:
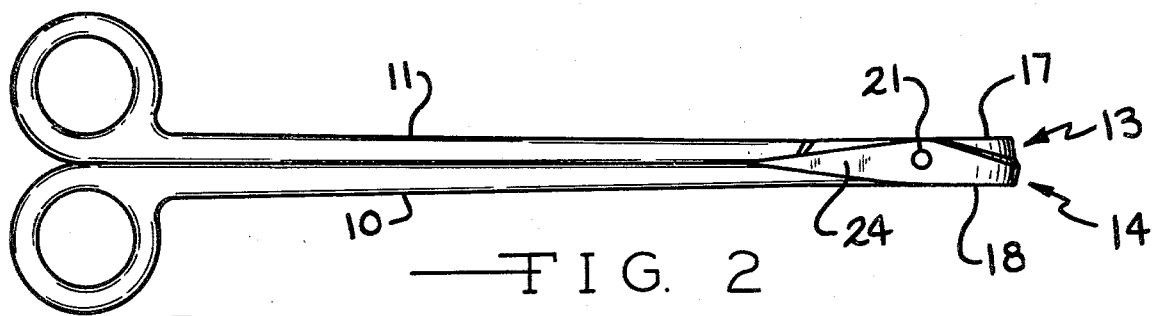
FIG. 2 is a side elevational view of the surgical scissors showing the blades in closed position.
Figure 3:
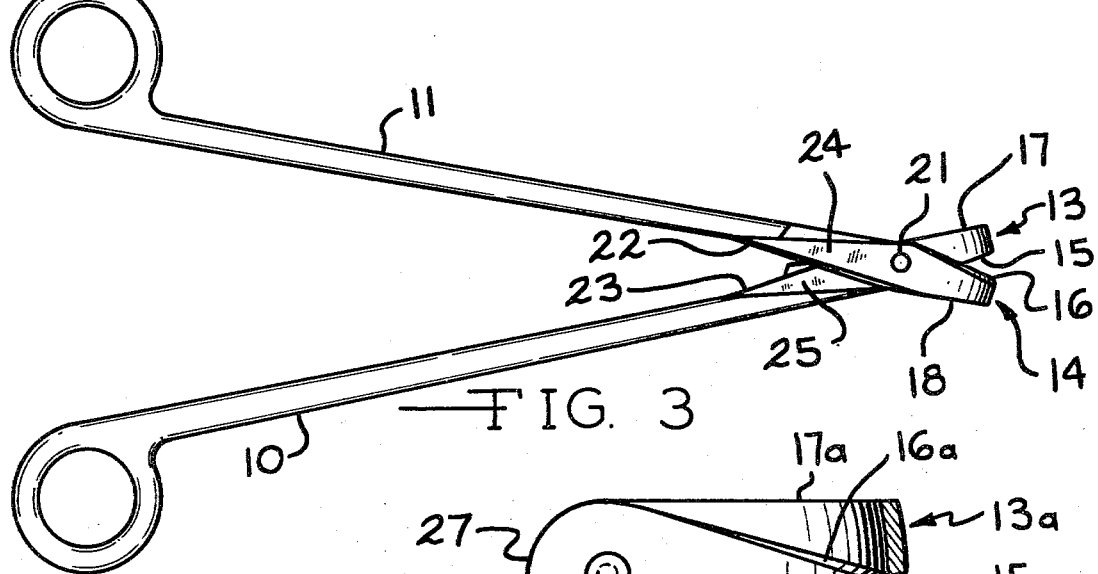
FIG. 3 is a side elevational view of the surgical scissors showing the blades in open position.
Figure 4:
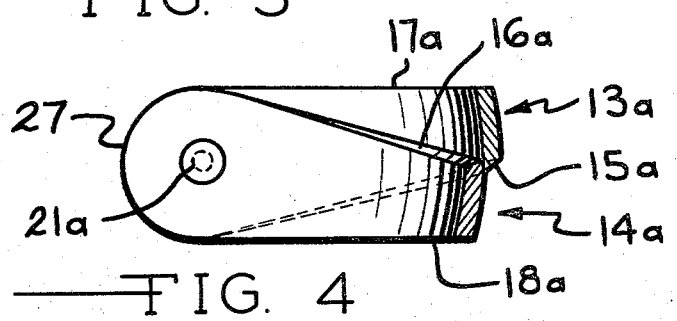
FIG. 4 is an enlarged sectional view of a modification.

Two additional cutting edges 22 and 23 on the hook-shaped ends cooperate to form cutting blades 24 and 25, respectively. The aligned pivots 20 and 21 extend along an axis which is in between the set of cutting blades 17 and 18 and the set of cutting blades 24 and 25. The cutting surfaces 22 and 23 are on the inside of the cutting blades 24 and 25 as on straight scissors and are in a cutting plane 26 which is generally parallel to the axis 12. In an instrument in which only the blades 17 and 18 need be used, the cutting blades 24 and 25 can be omitted by forming the hooked-shaped ends along the edge 27 shown in the modification in FIG. 4. Reference numbers in FIG. 4 which are similar to those in FIGS. 1–3 refer to parts alike in structure and function.

In operation, for example, in the retromolar pad area in the mouth which is almost vertical, the scissors are inserted with the handle members 10 and 11 generally horizontal. The cutting blades 17 and 18 are moved about the cutting axis 19 to remove vertically arranged tissue. Also in operation, for example, when tissue in the third molar area cannot be properly trimmed or sutures cut by conventional straight scissors due to their positions, the reverse cutting blades 24 and 25 are used; the scissors are inserted with the handle members 10 and 11 generally horizontal and the reverse cutting blades 24 and 25 are located between the cheek and the third molar and moved in the cutting plane 26.

The scissors can be in a variety of sizes and used by surgeons in procedures where removal of tissue is made simpler. For example, if the tissue to be removed is in an area of limited access immediately below the surgeon, instead of the surgeon changing his position or having someone across from him perform the excision, the reverse scissors can be used.

It is to be understood that the above description is illustrative of this invention and that various modifications thereof can be utilized without departing from its spirit and scope.

I claim:

1. A pair of surgical scissors comprising two handle members extending along a first axis and each having a hook-shaped end carrying a cutting edge, and two aligned pivots pivotally connecting the hook-shaped ends, the cutting edges cooperating to form two blades for cutting in a plane which is generally perpendicular to the first axis.

2. A pair of surgical scissors comprising two handle members extending along a first axis and each having a hook-shaped end carrying two cutting edges, and two aligned pivots pivotally connecting the hook-shaped ends, the cutting edges cooperating to form first cutting blades for cutting in a plane generally perpendicular to the first axis and second cutting blades in a cutting plane which is generally parallel to the first axis, the aligned pivots extending along an axis which is between the first and second cutting blades.

3. A pair of surgical scissors comprising two handle members which are joined at a first pivot and extend along a first axis, each having a hook-shaped end, the bent portions of the hook-shaped ends having blade edges which cooperate to cut in a plane generally perpendicular to the first axis, and said hook-shaped ends also having blades which are joined at a second pivot aligned with said first pivot and which blades form reverse-acting scissors extending rearward past the axis of said second pivot.

* * * * *